United States Patent [19]

Karll et al.

[11] 3,954,849

[45] May 4, 1976

[54] PREPARATION OF ALKENYL SULFONATES

[75] Inventors: Robert E. Karll; Dennis G. Petrille, both of Batavia, Ill.; Edward W. Heffern, Tulsa, Okla.

[73] Assignee: Standard Oil Company, Chicago, Ill.

[22] Filed: Dec. 5, 1974

[21] Appl. No.: 529,811

Related U.S. Application Data

[63] Continuation-in-part of Ser. No. 316,880, Dec. 20, 1972, abandoned.

[52] U.S. Cl. .......................... 260/504 S; 260/513 T
[51] Int. Cl.² ......................................... C07B 13/00
[58] Field of Search .......... 260/513 R, 504 S, 513 T

[56] References Cited
UNITED STATES PATENTS

| | | | |
|---|---|---|---|
| 3,420,875 | 1/1969 | Di Salvo et al. | 260/513 |
| 3,496,225 | 2/1970 | Logan et al. | 260/513 |

*Primary Examiner*—James O. Thomas, Jr.
*Assistant Examiner*—A. Siegel
*Attorney, Agent, or Firm*—Edwin C. Lehner; Arthur G. Gilkes; William T. McClain

[57] ABSTRACT

Treatment of oil-soluble viscous liquid propene or butene polymers having a number average molecular weight of about 250–500 with gaseous sulfur trioxide in falling-film or static reactors yields acidic sulfonation products comprising alkenyl sulfonic acids and polymer sultones. Two-stage neutralization of the sulfonation product with ammonia or sodium hydroxide reduces the sultone content and increases the sulfonate content in the neutralized product.

4 Claims, No Drawings

PREPARATION OF ALKENYL SULFONATES

CROSS-REFERENCE TO RELATED APPLICATION

This application is a continuation-in-part of U.S. application Ser. No. 316,880, filed Dec. 20, 1972, now abandoned.

FIELD OF THE INVENTION

This invention relates to a method for preparing oil-soluble ammonium or sodium alkenyl sulfonates wherein the alkenyl moiety is a propene or butene polymer having a number average molecular weight of about 250–500.

SUMMARY OF THE INVENTION

The present invention is a two-stage or two-step process for neutralizing acidic sulfonation products to form liquid neutralized products, having reduced sultone content, which are useful as surfactants in aqueous oil systems or as additives for petroleum products. In accordance with the invention, an acidic sulfonation product mixture comprising alkenyl sulfonic acids wherein the alkenyl moiety is a propene or butene polymer having a number average molecular weight of about 250 to about 500 and sultones of said polymer, obtained by continuously treating a viscous liquid oil-soluble propene or butene polymer having a number average molecular weight of about 250 to about 500 with gaseous sulfur trioxide in a falling film reactor or in a static reactor having interfacial surface generating means, is neutralized with ammonia or sodium hydroxide to form a liquid neutralized product mixture having a reduced sultone content by the process comprising: first treating at atmospheric pressure said sulfonation product mixture at a temperature in the range of from about 100° to about 170°F. with an amount of ammonia or aqueous sodium hydroxide sufficent to neutralize said sulfonic acid and provide a basic mixture comprising sodium or ammonium alkenyl sulfonates and said polymer sultones; and thereafter heating at atmospheric pressure said basic mixture to a temperature in the range of from about 290° to about 340°F. to remove any water in said mixture and holding, while maintaining the basicity of said mixture above pH 7, the anhydrous basic mixture at said temperature and pressure for a period of time sufficient to reduce the sultone content of said basic mixture and form said neutralized product mixture comprising ammonium or sodium alkenyl sulfonates.

The acidic sulfonation product is a complex mixture comprising alkenyl sulfonic acids containing mono-, di- and poly-sulfonic acid groups, sultones, sulfur-containing by-products and unreacted polymer which is a carrier or vehicle diluent for the sulfonated materials. The sulfonation product may be first purified to remove the precursors of oil-insoluble materials that form on neutralization when a substantially pure oil-soluble neutralized product is desired. When a purified acidic sulfonation product is neutralized in accordance with this invention, it has been found that maximum yield of the alkenyl sulfonate is obtained with ammonia. Neutralization of the unpurified acidic sulfonation product with either ammonia or sodium hydroxide gives equivalent yields.

For preparation of the acidic sulfonation product, either falling-film reactors or static reactors can be used for the continuous sulfonation of the polymers. Falling-film reactors are well known in the sulfonation art as exemplified by U.S. Pat. No. 3,328,460. Liquid mixers having no moving parts are known. Generally, they comprise a mixing chamber provided with partitions or guide members to successively divide and reunite the stream of flowing liquid therein, that is, have interfacial surface generating means. U.S. Pat. Nos. 3,051,452; 3,051,453; 3,195,865; 3,206,170 and 3,286,992 are illustrative of the type of mixers that are suitable for use as static reactors to form crude sulfonation mixtures.

DESCRIPTION OF THE PREFERRED EMBODIMENTS

Example 1

Liquid polybutene (butene polymer having a number average molecular weight of about 340) was introduced into a slot-type falling-film reactor of the type described in U.S. Pat. No. 3,328,460 at a rate of 388 pounds per hour. The reactor was 22 feet long with a slot dimension of ⅝ inch by 24 inches. The film temperature in the reactor was 80–122°F. Gaseous sulfur trioxide diluted with air at a molar rate of 1.93 mols per mol of polybutene, was introduced cocurrently to the film in the reactor at a rate of 170 pounds per hour and air rate of 900 cubic feet per minute at 18 psig. Liquid residence time was about 125 to 150 seconds in the reactor. The crude acid mix from the reactor had a total activity of about 72 weight percent, contained about 46 weight percent sulfonic acid, about 7 weight percent hexane-insoluble sludge, and about 19 weight percent sultone.

The crude acid mix was diluted with an equal volume of hexane and 10 weight percent water. The aqueous mixture was held with agitation at 130–140°F. for 1 hour in a holding-settling tank. After a 2 hour settling period, the aqueous phase was drawn off and the hexane-acid phase, containing a mixture of sulfonic acids and sultones, was transferred to a reactor for neutralization.

Neutralization at atmospheric pressure of the sulfonic acid-sultone mixture in hexane was effected by first introducing anhydrous ammonia into the mixture at a rate of 2 cubic feet per hour per gallon of hexane mixture while maintaining temperature of the mixture below 150°F. until a color change of from black to amber was noted which indicated neutralization of the sulfonic acid. At that point the ammonia rate was reduced to 0.5 cubic foot per hour per gallon and the temperature of the mixture raised with removal of hexane and water to a temperature of 310°F., and the anhydrous mixture was held at atmospheric pressure and at 310°F. with continued introduction of ammonia for 2 hours to maintain the anhydrous mixture basic and reduce the sultone content, at which time the treatment was terminated. The neutralized product containing 64.6 weight percent ammonium alkenyl sulfonate and 2.8 weight percent sultone was a crystal clear liquid that did not require filtration.

The term "activity" as used herein refers to the percent of polar material present in the crude sulfonation reaction reaction and neutralized products by silica gel chromotography. A 2 gram sample is diluted with 20 ml hexane and deposited at room temperature on a 40 gram silica gel column having a 0.75 inch diameter. The unreacted polymer is eluted from the column with 250 ml of hexane and weight obtained after evaporation of hexane. Sample weight minus weight of polymer yields total activity in sample. Sultone content is obtained by elution with 250 ml of chloroform. Sulfonate content is total activity minus sultone.

Example II

Liquid polybutene having a number average molecular weight of about 340 was treated with gaseous sulfur trioxide in a static reactor of the type described in U.S. Pat. No. 3,286,992 to give a sulfonation product mixture having an activity of 89.3 weight percent and containing 35.9 weight percent hexane-insoluble sludge. The static reactor, containing 21 elements (interfacial surface generating means), has an I.D. of ¼ inch and is 9 inches in length. A liquid stream of the polybutene flowing at a rate of 1.68 grams per minute was introduced cocurrently with an air stream, flowing at a rate of 20,000 cc per minute, containing 0.70 cc per minute of sulfur trioxide into the static reactor. Sulfonation product was discharged from the reactor at a rate of 2.10 gram per minute. The molar ratio of sulfur trioxide to polymer being about 3.4 in the flowing streams. To the sulfonation product mixture was added and equal volume of hexane and 10 weight percent water. the aqueous mixture was heated to and held at 140°F., with stirring, for 1 hour, then settled for 1 hour and phases separated. The hexane phase was then treated with ammonia as in example I. The neutralized product was a crystal clear liquid, having an activity of 76%, free of oil-insoluble material and did not require filtration.

Example III

An acidic sulfonation product having a total activity of 90 weight percent and containing 40 weight percent hexane-insoluble material, 19 weight percent sultone and 10 weight percent unreacted polymer was obtained using the polybutene described in example I by the process described in example II using the static reactor. The total sulfonation product was treated with ammonia as described in example I forming a homogeneous heavy viscous neutralized liquid product containing 61 weight percent ammonium sulfonate and 4 weight percent sultone.

Example IV

A sulfonation product that was formed by treating the polymer of example I by the procedure described in example II contained 26 weight percent hexane-insoluble sludge, about 19 weight percent sultone and had a total activity of 80 weight percent. The sulfonation product diluted with an equal volume of hexane was neutralized with sodium hydroxide by first adding small incremental portions of a 50% sodium hydroxide solution to the diluted mixture being maintained at atmospheric pressure and at a temperature of about 120°–130°F. until color changed from a deep purple to dark brown at which time the pH of the mixture was 11. The basic mixture was then heated at atmospheric pressure with removal of hexane and water to a temperature of 320°F., and the anhydrous basic mixture held for 2 hours at said temperature and pressure and then filtered. The liquid product had an activity of 80% and a sultone content of 3.5 weight percent.

Cleavage of the sultone ring under the conditions required in the second step of the process of this invention yields oil-soluble neutralized products substantially free of hydroxy alkyl sulfonates for the presence of such hydroxy-substituted sulfonates was not detected by infra-red analysis of the products.

We claim:

1. The process of neutralizing a sulfonation product mixture comprising alkenyl sulfonic acids wherein the alkenyl moiety is a propene or butene polymer having a number average molecular weight of about 250 to about 500 and sultones of said polymer with ammonia or sodium hydroxide, said sulfonation product mixture obtained by continuously treating a liquid propene or butene polymer having a number average molecular weight of about 250 to about 500 with gaseous sulfur trioxide which process comprises the steps of: first treating at atmospheric pressure said sulfonation product mixture at a temperature in the range of from about 100° to about 170°F with an amount of ammonia or aqueous sodium hydroxide sufficient to neutralize said sulfonic acid and provide a basic mixture comprising ammonium or sodium alkenyl sulfonates and said polymer sultones; and thereafter heating at atmospheric pressure said basic mixture to a temperature in the range of from about 290° to about 340°F to remove any water in said mixture and holding at atmospheric pressure, while maintaining the basicity of said mixture above pH 7, the anhydrous basic mixture at said temperature for a period of time sufficient to reduce the sultone content of said basic mixture and form additional alkenyl sulfonates whereby a liquid neutralized product mixture, substantially free of hydroxy alkyl sulfonates, comprising ammonium or sodium alkenyl sulfonates is obtained.

2. The process of claim 1 wherein said treating agent is sodium hydroxide.

3. The process of claim 1 wherein said treating agent is anhydrous ammonia.

4. The process of claim 1 wherein said polymer is polybutene having a number average molecular weight of about 340.

* * * * *